United States Patent [19]

Clair et al.

[11] Patent Number: 4,471,775
[45] Date of Patent: Sep. 18, 1984

[54] ENDOTRACHEAL TUBE CUFF SYNCHRONIZING SYSTEM

[76] Inventors: Michael W. Clair, 6643 Hesperia, Reseda, Calif. 91335; Donald L. Ball, 10010 Independence, Chatsworth, Calif. 91311

[21] Appl. No.: 415,225

[22] Filed: Sep. 7, 1982

[51] Int. Cl.³ ............................................ A61M 16/00
[52] U.S. Cl. ........................... 128/205.24; 128/207.15
[58] Field of Search ...................... 128/207.15, 204.18, 128/204.19, 204.24, 204.26, 204.27, 204.28, 204.29, 205.14, 205.15, 205.24

[56] References Cited

U.S. PATENT DOCUMENTS 2,117,952  5/1938  Gourdon .......................... 128/205.24
3,754,550  8/1973  Kipling ............................ 128/205.24
4,285,340  8/1981  Gezari et al. .................... 128/207.15

Primary Examiner—Henry J. Recla
Attorney, Agent, or Firm—David O'Reilly

[57] ABSTRACT

A system and method for controlling the inflation and deflation of a balloon or cuff on an endotracheal tube comprised of a synchronizing valve connecting a gas supply to the cuff of the tube. The valve is in turn connected to pilot pressure from a volume ventilating pump which supplies oxygen-containing gas to the endotracheal tube. The pilot pressure from the volume ventilating pump operates the valve at the beginning of the inspiration cycle to inflate the cuff to a pressure controlled by an adjustable pressure regulator between a gas supply and the valve. During the expiration cycle the valve closes to connect the cuff to an exhaust to deflate the cuff to a predetermined minimum temperature controlled by another adjustable regulator. In this manner, inflation of the cuff and deflation of the cuff is synchronized with operation of the volume ventilating pump through the synchronizing control valve means. The pilot line pressure is supplied from the pilot line which also supplies pilot pressure to an exhalation valve to exhaust expirated air from the lungs of a patient.

11 Claims, 7 Drawing Figures

ENDOTRACHEAL TUBE CUFF SYNCHRONIZING SYSTEM

FIELD OF THE INVENTION

This invention relates to endotracheal tubes and more particularly relates to systems for controlling the inflation and deflation of an endotracheal tube cuff.

BACKGROUND OF THE INVENTION

Whenever a patient requires total respiratory support, he is connected to a positive pressure volume ventilating pump by means of a closed breathing circuit. A plastic or rubber tube, called an endotracheal tube, is inserted through the patient's mouth into his trachea to supply a prescribed volume of oxygen-containing gas from the volume ventilating pump. Near the end of the tube inserted into the trachea is a plastic balloon called a "cuff" which encircles the outside diameter of the tube. This cuff is inflated by means of a line bonded to or incorporated into the wall along the length of the tube. The cuff, when inflated, separates the upper airway or trachea from the closed breathing circuit. This allows precise delivery of a prescribed volume of oxygen-containing gas to the patient and prevents the aspiration of oral and/or gastric material into the trachea.

However, because the cuff must be constantly kept inflated, the amount of pressure it exerts on the delicate tracheal tissue becomes a critical factor. If the pressure is excessive, it prevents or restricts the flow of blood to the tracheal tissues and can cause necrosis (death) or serious damage to the tissue. This damage can lead to many immediate and long term medical problems.

For the reasons given above, it is advantageous to inflate the cuff to completely close off the trachea during delivery of the prescribed volume of gas (inspiration) and deflate the cuff to a minimum pressure during exhalation of the gas (expiration). The deflation of the cuff leaves just the minimum amount of pressure to prevent entrance of foreign bodies or aspiration into the trachea. These previous systems are directed towards management of the patient's airway and minimizing the cuff pressure during expiration. One of the forerunners of these systems utilizes a syringe to provide a prescribed volume of air to the cuff during inspiration and releases that volume of air during expiration. In this system, a nebulizer drive line is used to drive the syringe to provide a prescribed volume of air to the cuff. In other words, the volume of the syringe is pumped into and then released from the cuff cyclically. No attempt to regulate the cuff pressure in the exhalation cycle is attempted with this system. Various other systems use complicated valving mechanisms, but they are not generally synchronized with the operation of the volume ventilating pump. For this reason, none of the techniques now known or in use are totally satisfactory. They are either time consuming, hazardous to the patient or both and are, in any case, generally circumvented by poorly trained, overworked or inattentive staff members. The necessity of providing a good airway seal is paramount, regardless of the cuff pressure.

Therefore, it is one object of the present invention to provide a endotracheal tube cuff inflation and deflation control system which is synchronized with the volume ventilating pump.

Another object of the present invention is to provide an endotracheal tube cuff inflation and deflation system in which the maximum and minimum pressures are precisely regulated.

Still another object of the present invention is to provide a system for inflation and deflation of an endotracheal tube cuff which utilizes an exhalation valve pilot line.

Yet another object of the present invention is to provide a system for controlling inflation and deflation of an endotracheal tube cuff which provides a positive cutoff for maximum and minimum pressure of inflation of the cuff.

SUMMARY OF THE INVENTION

The purpose of the present invention is to provide a controlled inflation and deflation system for endotracheal tube cuffs which is synchronized with the delivery of air to a patient.

The purpose of the present invention are realized by a cuff inflation and deflation system synchronizer which takes advantage of a feature incorporated in every positive pressure volume ventilating pump system. That is, it takes advantage of the exhalation pilot pressure drive line. This pilot pressure drive line to the exhalation valve delivers air to an exhalation valve balloon just before the main ventilator volume is given. Along with the endotracheal tube cuff this provides for the closure of the breathing circuit during inspiration. With the synchronizer system of the present invention, the exhalation drive line flow is coupled to a valve means which responds to the flow by delivering an adjustable inflation pressure to the endotracheal tube cuff. Thus, when the volume ventilating pump cycles on, the exhalation balloon and endotracheal tube cuff are inflated simultaneously. When the volume ventilating pump cycles off, both the balloon and the cuff simultaneously deflate. Since a seal is necessary in the trachea, even during passive exhalation, means are provided to allow a residual minimum pressure to be maintained in the cuff. This minimum pressure is adjusted by means of a regulator or a valve having a predetermined cutoff. The higher pressure also regulated therefore is exerted upon the tracheal tissue only when it is necessary, which is during delivery of air to the patient or inspiration.

The purposes of the invention are also realized by providing a positively controlled valve between a gas supply and the inflatable cuff on the endotracheal tube. This valve means is controlled by pilot pressure from the volume ventilating pump means. The valve is cycled on at the beginning of delivery of air from the volume ventilating pump to a patient to inflate the cuff to a predetermined maximum pressure. An adjustable regulator in the line delivering gas through the valve to the endotracheal tube cuff precisely controls the maximum pressure to which the cuff is inflated. During expiration, the pilot line pressure drops to a low pressure closing the valve means and allowing the endotracheal tube cuff to exhaust through the valve to deflate the cuff to a predetermined pressure. This predetermined minimum pressure is controlled either by a second positively controlled valve which cuts off at a predetermined minimum pressure, or by another pressure regulator which controls the operation of a deflation valve. The above and other features of the invention will be fully understood from the following detailed description and the accompanying drawings in which:

DETAILED DESCRIPTION OF THE INVENTION

Figure 1:
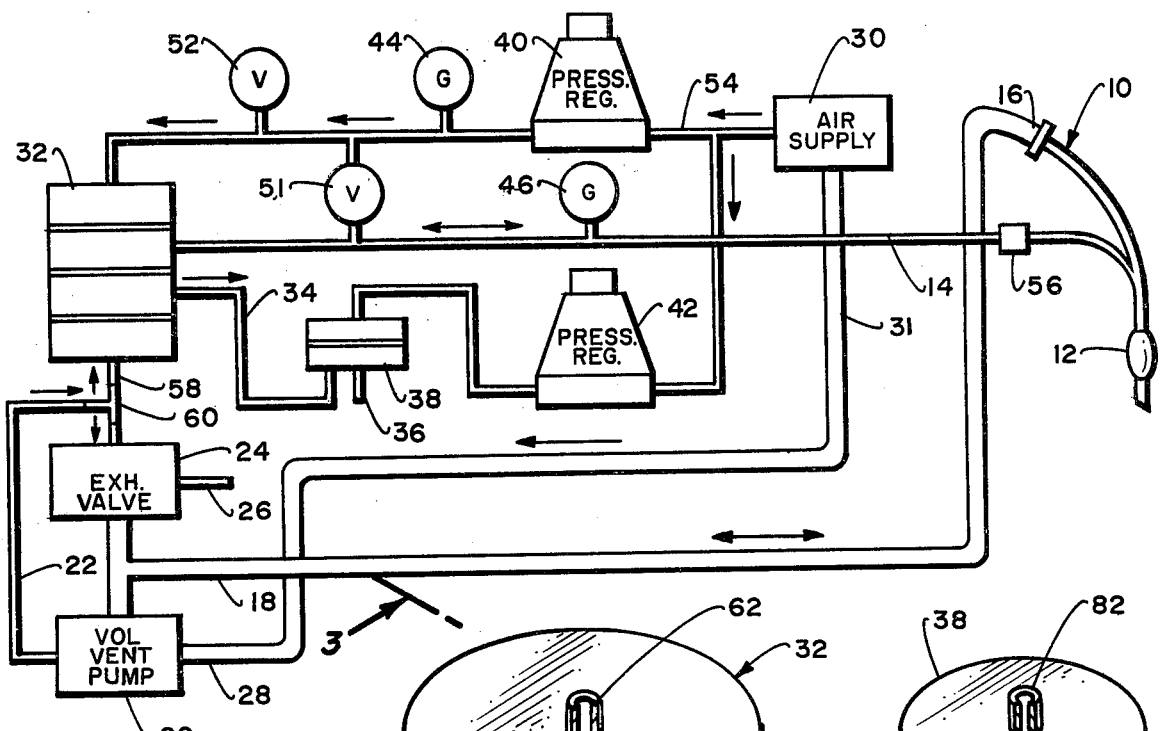
FIG. 1 is a simplified schematic diagram of the synchronized cuff inflation system according to the invention.

A schematic diagram illustrating the flow of gas to and from an endotracheal tube is illustrated in FIG. 1. In the usual breathing system, an endotracheal tube 10 is inserted through the mouth of a patient into his windpipe or trachea just beyond his vocal cords and the endotracheal tube cuff 12 is inflated. This cuff encircles the outside diameter of the tube as is known in the art and is inflated through a line 14 either bonded to the outside length of the tube or its integral in the wall of the tube. Fitting 16 is connected to line 18 from which air or an oxygen-containing gas is supplied by a positive pressure volume ventilating pump 20. With the cuff 12 properly inflated, the upper airway or trachea is separated from the closed breathing circuit. This allows precise delivery of a prescribed amount of air from the volume ventilating pump 20 through line 18 connected to fitting 16 on endotracheal tube 10. The cuff 12 also prevents the aspiration of oral and/or gastric material into the trachea during inspiration or expiration.

The inspiration/expiration cycle operates as follows. The volume ventilating pump 20 delivers a prescribed, precisely controlled amount of air to the endotracheal tube 10 which is delivered to the lungs of a patient. Just in advance of the main flow of gas to the patient, a flow of gas is directed, via pilot line 22, to inflate a balloon in exhalation valve 24, closing the valve to prevent the escape of main flow gas to the atmosphere. The volume ventilating pump 20 then shuts off, causing pilot pressure in line 22 to drop, deflating the balloon in the exhalation valve 24, allowing the valve to open. The air is then exhaled through endotracheal tube 10, line 18, exhalation valve 24, to exhaust line 26. The cuff 12 must be constantly kept inflated during the inspiration and expiration. However, during expiration (i.e. exhalation) the amount of pressure in the cuff is less critical and only a minimum amount of pressure is necessary to simply close off the trachea to prevent the aspiration of oral or gastric material. However, because the cuff must be constantly kept inflated, the amount of pressure it exerts on delicate tracheal tissue is critical. If the pressure applied by the cuff 12 is excessive it will restrict or prevent the flow of blood to the tissue and cause the tissue to die (tissue necrosis) or be damaged. This damage or tissue necrosis can obviously lead to numerous immediate and long term medical problems. The air or oxygen-containing gas is supplied to line 28 from the usual hospital supply 30 through line 31.

There has been much attention devoted to management of the patient's airway or trachea which is directed toward minimizing the pressure in cuff 12 to prevent any tissue necrosis. However, none of the techniques in use today are totally satisfactory. They are either complicated and costly or much too simple to operate effectively. For that reason the present invention utilizes a synchronized cuff inflation system which takes advantage of a feature incorporated in the volume ventilating pump system 20. That is, namely, the exhalation drive line 22 providing pressure to exhalation valve 24. This line delivers air to a balloon in exhalation valve 24 just before the main ventilator volume is delivered to the endotracheal tube 10 through line 18.

The system is comprised of a positive acting synchronizing valve 32 connected to an air supply which is preferably the same hospital air supply 30 which supplies air to the volume ventilating pump 20. The synchronizing valve 32 controls the flow of air to line 14 to inflate the cuff 12 just before the main volume ventilator pump delivers its prescribed volume of air to line 18. On exhalation the synchronizing valve 32 deflates the cuff 12 to a precisely controlled minimum pressure by exhausting air through the valve to line 34 to exhaust line 36 through deflation valve 38.

The inflation pressure and deflation pressure are precisely controlled by pressure regulators 40 and 42. Pressure regulator 40 adjusts the maximum pressure to which cuff 12 can be inflated through synchronizer 32 while regulator 42 controls deflation pressure by exerting control on deflation valve 38. Gages 44 and 46 provide an indication of the pressure on gas delivery line 50 and cuff inflation/deflation line 14. A relief valve 52 is placed in air delivery line 50 to prevent any abnormally high pressures should there be a failure of any kind of pressure regulator 40.

To initially set up the synchronizing system for inflation and deflation of cuff 12, the pressure regulator 40 is connected to oxygen in line 54 attached to hospital oxgen supply 30, typically operating at approximately 50 Psi. The cuff 12 is then connected to line 14 through a cuff connector 56. Pilot pressure for the synchronizing valve 32 is then provided by connecting line 58 to the exhalation drive line pilot pressure line 22, by means of a coupling or tee 60. Thus, pilot pressure is provided for the exhalation valve 24 and the synchronizing valve 32 from the exhalation drive line pilot pressure through tee 60. This synchronizes operation of the synchronizing valve 32 with the exhalation valve 24 and the prescribed, precise delivery of a volume of air from volume ventilating pump 20. Therefore, by a simple mechanical connection to the pilot pressure from the volume ventilating pump accurate positive control of inflation and deflation of the endotracheal tube cuff 12 is provided through the synchronizing valve 32.

Figure 2:
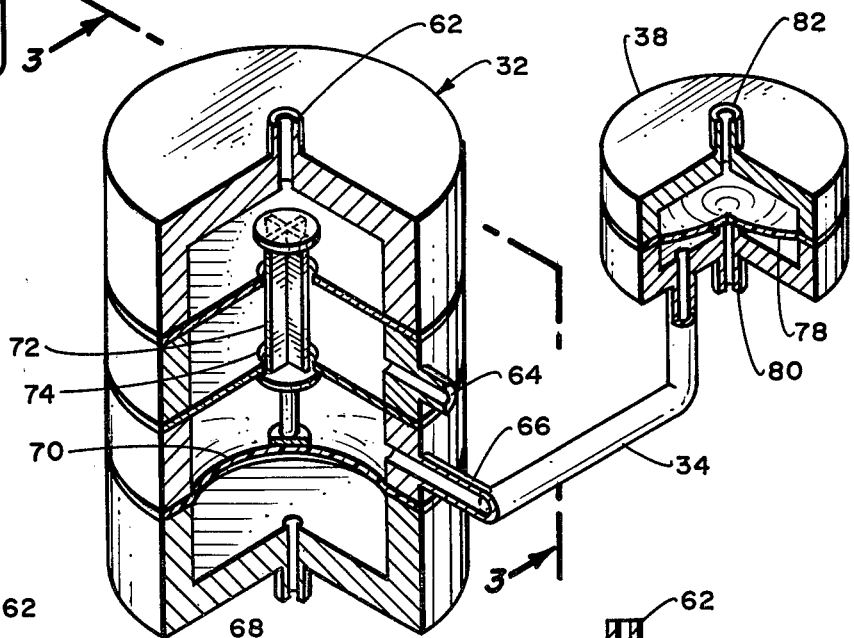
FIG. 2 is a perspective view of the synchronizing valve and deflation valve.

Preferably, the synchronizing valve 32 is a positive acting diaphragm valve as illustrated in FIG. 2. This positive acting diaphragm valve has an inlet port 62 and two outlet ports 64 and 66. Another inlet 68 is provided for connection to pilot pressure line 58 to activate the diaphragm 70 connected to the valve rod assembly 72. Outlet 64 will be connected to cuff inflation/deflation line 14. When the diaphragm 70 is in the rest position outlet 64 is connected to outlet 66 through aperture 74 around valve rod assembly 72. This provides exhaust for the cuff 12. That is, outlet port 64 is actually a two-way port for flow of air to and from endotracheal cuff 12 for inflation and deflation and outlet port 66 is an exhaust port for releasing air during deflation of the cuff 12.

Figure 3:
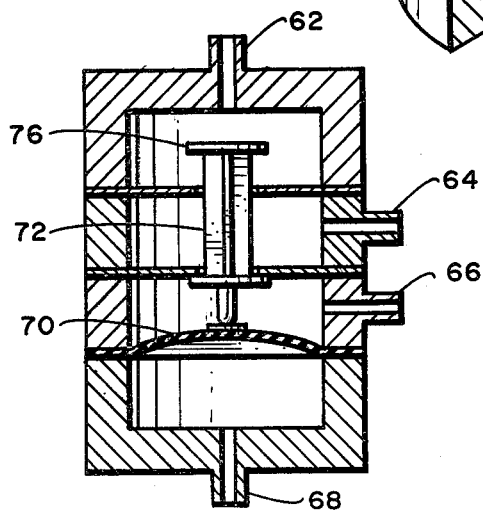
FIGS. 3 and 4 illustrate the operation of the synchronizing valve in the cuff inflation and deflation cycles respectively.
Figure 4:
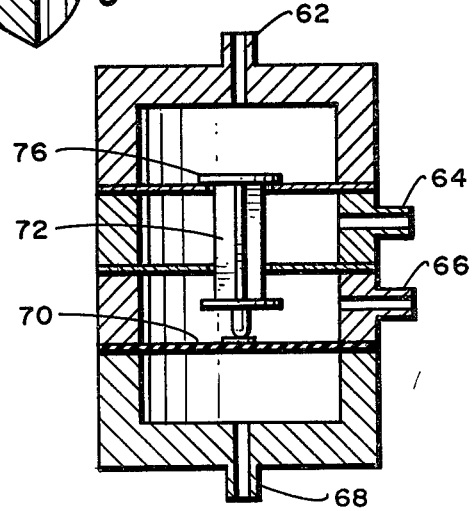

The operation of the synchronizing valve is illustrated in FIGS. 3 and 4. The operation of the valve to inflate the cuff 12 is shown in FIG. 3 while deflation of the cuff is shown in FIG. 4. At the start of the inhalation (inspiration) cycle the valve 32 is in the normal position shown in FIG. 4 with gas pressure shut off from the cuff 12 and the cuff is opened to exhaust line 34 connected to outlet 66. At this point, the diaphragm 70 is at rest. When pilot line 22 goes high (i.e. pilot pressure on lines 22, tee 60 and line 58 connected to pilot pressure inlet 68) the diphragm 70 will expand, moving the valve rod 72 up connecting inlet 62 with outlet 64. As this happens, the cuff 12 is cut off from exhaust 66 and gas is allowed to pass from inlet 62 to outlet 64 to inflate the cuff. The size of the diaphragm 70 is such that the pilot pressure on inlet 68 will overcome the gas pressure over the smaller area 76 at the top of valve rod 72.

When pilot pressure drops to a low level or near zero, the diaphragm 70 collapses and returns to the rest position as shown in FIG. 4, allowing the valve assembly rod 72 to return to the normal position cutting off the flow of gas to the cuff and connecting it to exhaust line 34 through outlet 66. This will cause the cuff to deflate.

The amount of deflation is controlled by deflation valve 38. Deflation valve 38 also has a diphragm 78 closing outlet 80 from exhaust line 34 connected to outlet 66. When the synchronizing valve 32 is in the position illustrated in FIG. 3 to inflate the cuff, diaphragm 78 in deflation valve 38 closes outlet 80. When pilot pressure goes low and diphragm 70 relaxes, exhaust line 34 is then connected to the cuff through the synchronizing valve 32. The exhausting gas from the cuff 34 will expand the diaphragm 78 in deflation valve 38 allowing the cuff gas to exhaust through outlet 80. By selecting a diaphragm 78 which will expand at the minimum pressure, the minimum pressure in the cuff 12 can be precisely controlled. However, as an alternative, inlet 82 is provided to the deflation valve 38 to provide further precise control of minimum cuff pressure as will be described in greater detail hereinafter.

As a further alternative, the deflation valve 38 could be a precisely controlled needle value which will slowly deflate the cuff 12 to a minimum pressure before synchronizing valve 32 is operated to reinflate the cuff. However, a needle valve, while providing control, may not be as precise as desired.

Figure 5:
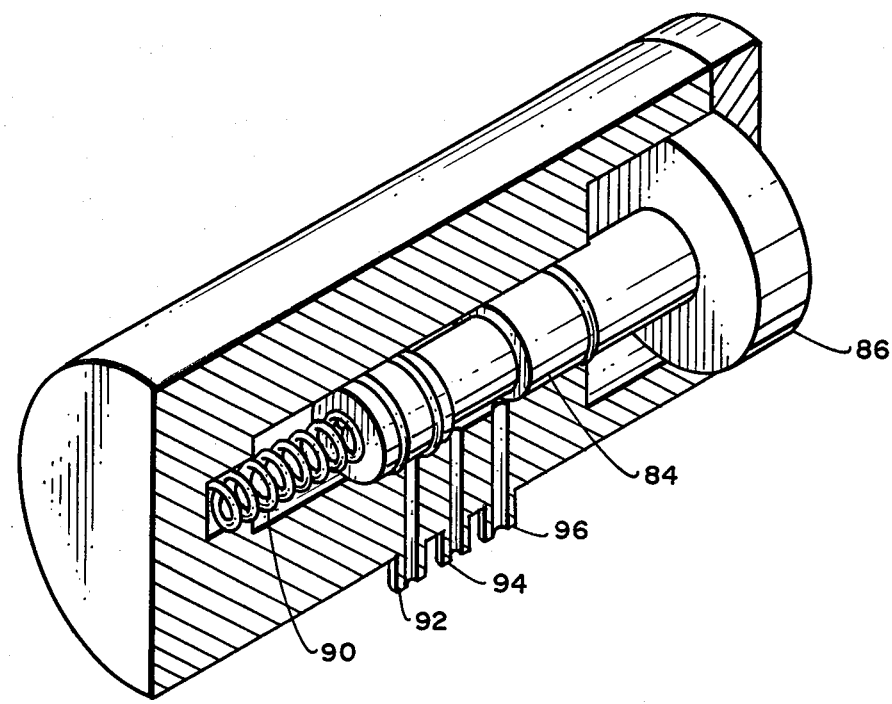
FIG 5. is a sectional view of an alternate construction for the synchronizing valve.
Figure 6:
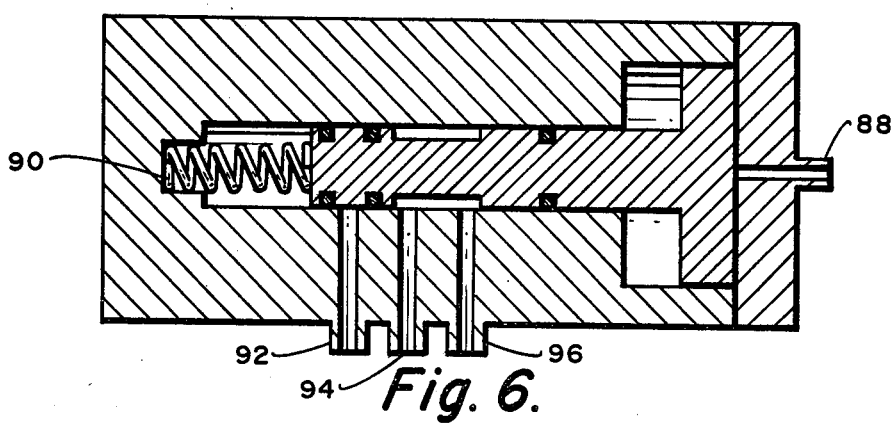
FIGS. 6 and 7 illustrate operation of the alternative synchronizing valve of FIG. 5 in the cuff inflation and deflation cycles respectively.
Figure 7:
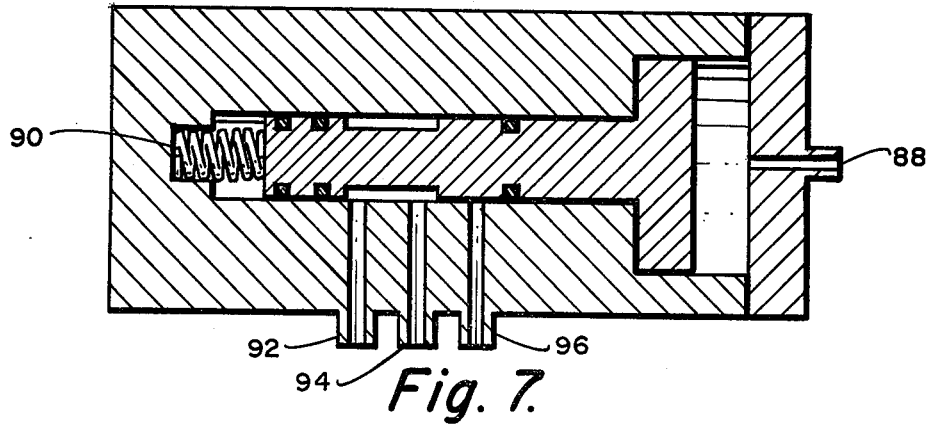

An alternate construction for the synchronizer valve is shown in FIGS. 5 through 7. This valve is an air operated spring return spool valve. Obviously, an air operated air return spool valve could be utilized, if desired. In this valve, a spool 84 having a piston 86 on one end is operated by air pressure connected to an inlet 88 (FIG. 6). The inlet 88 will be connected to pilot pressure line 58 for operation of the spool valve. The spring 90 returns the valve when pressure is removed from inlet 80. The ports 92, 94 and 96 provide for connections to the gas, cuff line and exhaust line respectively. Port 22 will be connected to gas supply line 50 while port 94 will be connected to cuff line 14. Port 96 will be connected to exhaust line 34.

In operation the valve will be in its normal position illustrated in FIG. 5 with spring 90 holding the piston 86 against the end of inlet 88 connected to the pilot pressure side of the valve. Thus, the cuff 12 will be connected to the exhaust 34 through ports 92 and 96. When pilot pressure is applied to line 58 connected to inlet 88, the pressure on piston 86 will overcome the force of the spring 90 to push the piston so that the gas inlet port 92 connected to line 50 is now connected to the cuff through port 94 as shown in FIG. 7. When the volume ventilating pump 20 stops and pilot pressure on port 88 goes low, the spring 90 will again push the piston to the normal position connecting the cuff 12 to the exhaust port 96.

The synchronizing system is initially set up as shown in the schematic diagram of FIG. 1. Calibration of the synchronizing system consists of opening a two-way bypass valve 51 allowing gas pressure to flow through the valve to the cuff 12. The pressure on the cuff 12 is then adjusted by means of adjustable pressure regulator 40 to the desired maximum. The two-way bypass valve 51 is then closed. With the cuff synchronizing valve 32 in operation, the deflation valve on the exhaust line 34 is adjusted to provide a desired minimum pressure to be maintained on the cuff during the exhalation cycle. This is accomplished by adjusting pressure regulator 42 (or the needle in the case of a needle valve) to provide an offsetting pressure to port 82 in deflation valve 38. This offsetting pressure will cause diaphragm 78 to close exhaust port 80 shutting off the exhaust when the cuff 12 reaches the desired minimum pressure.

The synchronizing system operates as follows. Just before the volume ventilating pump 20 delivers a prescribed volume of air to endotracheal tube 10 through line 18 the pilot pressure on line 22 will go high to close the exhalation valve 24. This same pilot pressure will be delivered to synchronizing valve 32 to connect cuff to gas supply line 54 causing the synchronizing valve to inflate the cuff to the present maximum pressure. The volume ventilating pump 20 will then deliver the patient's prescribed air volume. The volume ventilator pump will then stop and the pilot pressure on line 22 will then go to a low pressure or zero to begin the exhalation cycle. At this time the synchronizing valve 32 connects the cuff to the exhaust line 34 allowing the cuff to deflate to the minimum desired pressure. The cuff is only partially deflated, however, and keeps the trachea closed so that mucus accumulations above the cuff will not enter the patient's lungs. At this point, the entire cycle begins again.

Thus, there has been described a synchronizing system for synchronizing the inflation and deflation of a cuff on an endotracheal tube with the operation and delivery of a prescribed volume of air to a patient. The synchronizing system employs a positive acting valve synchronized with the operation of the volume ventilating pump by connecting the valve directly to the pilot pressure line which operates the exhalation valve.

This invention is not to be limited by the embodiment shown in the drawings and described in the description, which is given by way of example and not of limitation but only in accordance with the scope of the appended claims.

What is claimed is:

1. An inflation pressure synchronizing system for an inflatable cuff on an endotracheal tube comprising; an endotracheal tube having an inflatable cuff mounted thereon adjacent one end thereof;
    air supply means;
    ventilating pump means connecting said air supply means to the other end of said endotracheal tube to deliver a flow air to a patient during an inhalation cycle and prevent the flow of air to a patient during an exhalation cycle;
    exhalation valve means connected to said other end of said endotracheal tube;

an exhalation drive line connecting said exhalation valve means to said ventilating pump means for closing said exhalation valve means when said ventilating pump is delivering air to a patient;

a positive acting multiple port synchronizing valve means connecting said air supply to said endotracheal tube cuff;

said synchronizing valve means having an inlet port connected to said air supply, an exhaust port for venting air from said endotracheal tube cuff and a two-way port, an air line connecting said endotracheal tube cuff to said two-way port, and positive acting switch means for alternately switching said synchronizing valve means from a first position with said exhaust port connected to said two-way port during an exhalation cycle for venting said endotracheal tube cuff, to a second position during an inhalation cycle connecting said inlet port to said two-way port to inflate said endotracheal tube cuff;

said positive acting switch means being connected to said exhalation drive line for operation synchronized with the closing and opening of said exhalation valve means;

pressure regulating means connected between said air supply and said inlet port for controlling the maximum inflation pressure of said endotracheal tube cuff;

minimum inflation pressure limiting means connected to said exhaust port for limiting the minimum inflation pressure of said endotracheal tube cuff;

whereby said endotracheal tube cuff inflation is at a predetermined maximum pressure during the inhalation portion of the ventilating pump cycle and is at the minimum inflation pressure at all other times; and bypass valve means for bypassing operation of said synchronizing valve means, if desired, connected between said air supply downstream of said pressure regulating means for regulating maximum pressure and said air line connecting said two-way port to said endotracheal tube cuff.

2. The system according to claim 1 in which said synchronizing valve is a diaphragm valve; said synchronizing valve having a control port for operating said diaphragm connected to said exhalation drive line.

3. The system according to claim 2 in which said synchronizing valve includes a valve rod means alternately operable to connect said inlet port and said exhaust port to said two-way port; said valve rod means being operated by said diaphragm; whereby when said diaphragm is expanded by pressure in said exhalation drive line said valve rod means is operated to connect said inlet port to said two-way port to inflate said endotracheal cuff to maximum pressure and relaxation of said diaphragm releases said valve rod means connecting said exhaust port to said two-way port to deflate said endotracheal tube cuff to minimum predetermined pressure.

4. The system according to claim 3 in which said minimum inflation pressure limiting means comprises an exhaust diaphragm valve connected to said exhaust port; said diaphragm valve having a diaphragm adapted to close an exhaust line from said exhaust port when said cuff reaches a predetermined minimum pressure.

5. The system according to claim 4 including an adjustable pressure regulating means connecting a pressurized gas supply means to said exhaust diaphragm valve whereby the predetermined minimum pressure can be varied by adjusting said adjustable pressure regulating means.

6. The system according to claim 2 in which said valve means comprises a valve which connects said cuff to said air supply means when said diaphragm is expanded and connects said cuff to an exhaust line when said diaphragm is relaxed.

7. The system according to claim 1 in which said synchronizing valve means comprises at least one spool valve means responsive to said exhalation drive line pressure.

8. The system according to claim 7 in which said spool valve means is an air operated spring return spool valve.

9. The system according 1 in which said minimum inflation pressure limiting means comprises an exhaust diaphragm valve connected to said exhaust port; said diaphragm valve having a diaphragm adapted to close an exhaust line from said exhaust port when said cuff reaches a predetermined minimum pressure.

10. The system according to claim 9 including an adjustable pressure regulating means connecting a pressurized gas supply means to said exhaust diaphragm valve whereby the predetermined minimum pressure can be varied by adjusting said adjustable pressure regulating means.

11. The system according to claim 1 in which said minimum inflation pressure limiting means comprises an exhaust diaphragm valve connected to said exhaust port; said diaphragm valve having a diaphragm adapted to close an exhaust line from said exhaust port when said cuff reaches a predetermined minimum pressure.

* * * * *